United States Patent [19]

Kuisma et al.

[11] 4,378,168
[45] Mar. 29, 1983

[54] DEW POINT DETECTION METHOD AND DEVICE

[75] Inventors: Heikki Kuisma, Helsinki; Tapio Wiik, Espoo, both of Finland

[73] Assignee: Vaisala Oy, Finland

[21] Appl. No.: 238,563

[22] Filed: Feb. 26, 1981

[30] Foreign Application Priority Data

Feb. 29, 1980 [FI] Finland .................................. 800623

[51] Int. Cl.$^3$ ........................................... G01N 25/68
[52] U.S. Cl. ........................................ 374/28; 73/599
[58] Field of Search ................... 73/17 A, 597, 599; 310/313 B, 313 R; 374/28

[56] References Cited

U.S. PATENT DOCUMENTS 3,293,901  12/1966  Van Scoyoc et al. .............. 73/17 A
4,312,228   1/1982  Wohltjen ............................ 73/599

FOREIGN PATENT DOCUMENTS 52-96406  2/1977  Japan ................................ 73/17 A Primary Examiner—Herbert Goldstein
Attorney, Agent, or Firm—Steinberg & Raskin

[57] ABSTRACT

A piezoelectric sensor consists of material for transmitting elastic waves and has a surface subjected to the condensation and presence of dew and liquid to be detected. A wave producing device includes a transmitter for producing an acoustic surface wave on the surface in conjunction with piezoelectric phenomena of the sensor. A detector includes a receiver for receiving the wave after transmission thereof across the surface. The wave is variably attenuated in transmission between the transmitter and receiver in accordance with dew or liquid on the surface. A measuring device measures the attenuation of the detected wave and thereby indicates the dew point or presence of liquid on the surface.

23 Claims, 10 Drawing Figures

DEW POINT DETECTION METHOD AND DEVICE

BACKGROUND OF THE INVENTION

The present invention relates to a dew point detection method and device.

Several methods for the detection of a dew point are known. Among the most important methods are the optical method, in which the condensed moisture changes the reflection properties of a mirror, the radioactive method, in which the condensed moisture changes absorption of $\alpha$ or $\beta$ radiation, and the capacity/resistance method, in which the condensed moisture changes the capacity/resistance of a finger pattern on a surface.

There are, however, a few drawbacks in previously known methods, which, among other things, have made the present invention important. A drawback of the optical method is that the mirror is liable to get dirty, and, in corroding surroundings, be corroded. A mirror-like ice can also result in erroneous readings. In the radioactive method, or the like, a radiation source and sensitive detector is required, which makes it expensive to undertake the method.

SUMMARY OF THE INVENTION

The principal object of the invention is to provide a method and device for dew point detection which overcome the drawbacks of the known devices.

An object of the invention is to provide a dew point detection method and device wherein the sensor consists of very stable material, thereby avoiding corrosion problems.

Another object of the invention is to provide a dew point detection method and device wherein the sensor may be used at high temperatures.

Still another object of the invention is to provide a method and device for dew point detection wherein the surface of the sensor may be cleaned by heating it momentarily to a high temperature. This is especially advantageous and necessary when the humidity of smoke or gases is measured.

Yet another object of the invention is to provide a method and device for dew point detection whereby it is possible to detect the change of attenuation caused by condensation, independently of the background level caused by possible contamination. The operation should then by cyclic, or use must be made of a comparing unit in which the condensation is prevented. It is difficult to carry out a similar function, for example, in optical dew point detection.

In order to eliminate the drawbacks of the known devices and methods and to attain the foregoing objects, in the method and device of the invention, the presence of dew, or other similar liquid, is detected by a piezoelectric, or similar sensor. The piezoelectric, or similar, sensor has a surface on which acoustic waves are created, and which is subjected to the condensation or presence of the dew or liquid being detected. The condensation or presence is detected by measuring a parameter associated with the acoustic surface waves.

The principal feature of the device of the invention is that the apparatus comprises a substrate, in which the surface wave can proceed, and structures on the surface of the substrate necessary for the creation, and possibly detection, of the surface wave. The function of the structures is based on piezoelectric properties of the substrate, or a material combined with it. The structures comprise one or more electrode patterns consisting of electrically conducting material. There are contacts in the electrode patterns through which the alternating electrical energy or power is fed into, and possibly derived from, the sensor.

In the method of the invention, the condensed moisture alters the elastic properties of the surface of the material, and this alteration is detected by means of an acoustic surface wave, or SAW, traversing the surface which acts as a sensor. The condensed moisture causes, for example, a change in the attenuation or transit time of the surface wave.

The substrate of the sensor need not be piezoelectric material. It is sufficient that the substrate consist of a material in which the acoustic surface wave may be transmitted. In the alternative structure, the surface wave is created by piezoelectric material such as, for example, piezoelectric film, attached to the substrate.

In accordance with the invention, when detecting a dew point, the acoustic surface wave may be directly created by quartz due to a piezoelectric phenomenon. The same phenomenon may be used for the detection of the wave. There are several known structures for the provision of switch-over from an electric field to an acoustic surface wave. In a commonly used structure, the electric field required for the creation of the wave is produced by interlaced metal electrodes manufactured by thin-film technology and photolithography.

The physical background of the invention is briefly reviewed, as follows. An acoustic surface wave is attenuated, in interaction with thermal oscillations or vibrations in the material, by scattering from the non-continuity points of the surface, and in the medium coupling.

The change of attenuation aspect of the method of the invention is based on the last-mentioned two phenomena. As the speed of an acoustic wave is considerably slower in liquid than in solid materials, these last-mentioned attenuation types are, in the case of condensed water, particularly strong.

BRIEF DESCRIPTION OF THE DRAWINGS

For a fuller understanding of the invention, reference is had to the following description taken in connection with the accompanying drawings, in which.

DESCRIPTION OF PREFERRED EMBODIMENTS

Figure 1:
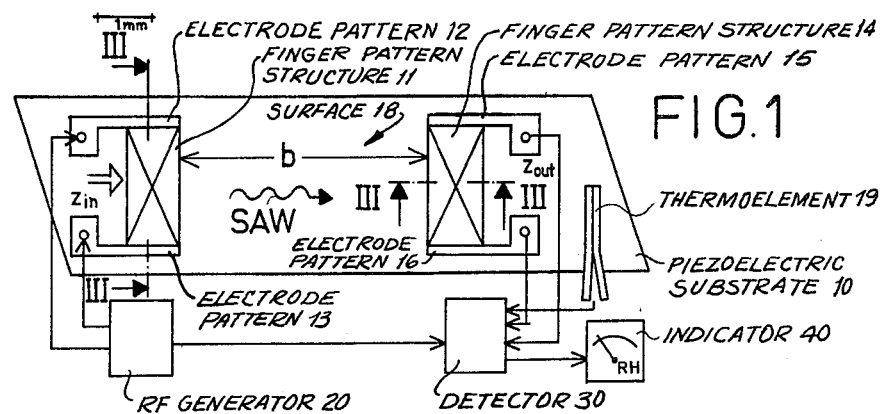
FIG. 1 is a schematic diagram of an embodiment of a device for undertaking the method of the invention.
Figure 2:
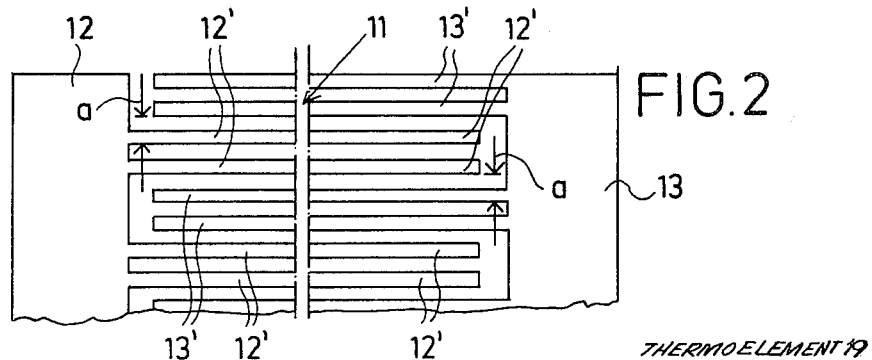
FIG. 2 is a schematic diagram, on an enlarged scale, of an embodiment of the surface pattern of the surface wave converter of the device of the invention.
Figure 3:
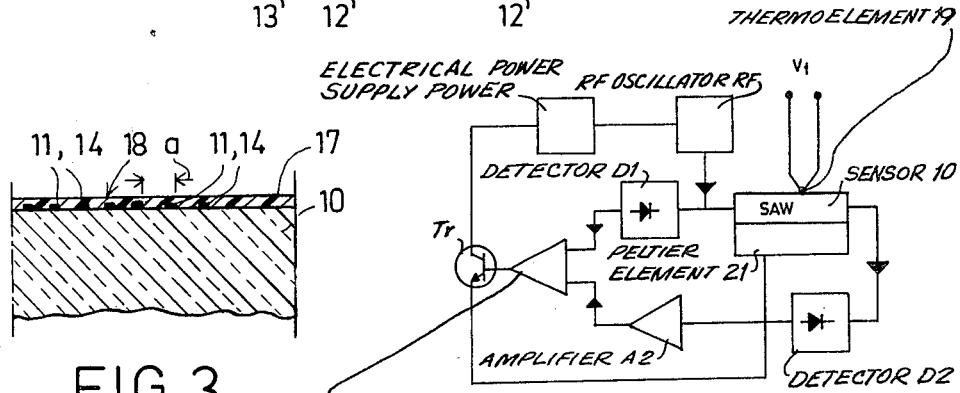
FIG. 3 is part of a sectional view, on an enlarged scale, taken along the lines III—III of FIG. 1.

As shown in FIG. 1, electrode patterns 12 and 13, with the finger pattern structure 11 between them, are produced by metallization of the surface of the piezoelectric substrate 10, on the transmitter side. On the receiver side, there are electrode patterns 15 and 16 and a finger pattern 14, similar to the finger pattern structure 11, between them, produced in the same manner. FIG. 2 is a more detailed illustration of the finger pattern structures 11 and 14. The finger pattern structures have interlaced strips 12' and 13' adjoining electrodes 12 and 13 in groups of two. The distance between the strips 12' and 13' in the proceeding direction A of the surface wave is indicated by a. The finger patterns 11 and 14 are protected, for example, by a protective layer 17 of SiO$_2$ having a thickness of 1000 to 3000 A. The substrate 10 is, for example, a 0.5 mm thick layer of LiNbO$_3$, as shown in FIG. 3.

The distance between the finger pattern 11 of the transmitter side and the finger pattern 14 of the receiver side is indicated by b in FIG. 1. In this area, as well as in the area of the finger patterns 11 and 14, the acoustic surface wave SAW, proceeding from the transmitter side, having an impedance $Z_{in}$, to the receiver side, having an impedance $Z_{out}$, attenuates.

Electrical energy or power is fed from an RF generator 20 at a frequency of approximately 100 to 200 MHz, for example, to the finger pattern between the electrodes 12 and 13. This creates acoustic vibrations or oscillations in the piezoelectric substrate 10 which are transmitted to the receiver side, where, due to piezoelectric phenomena, an electric oscillation, detected by a detector 30, is produced between the electrodes 15 and 16.

The method of the invention is based upon the attenuation, for example, of an acoustic surface wave SAW between the transmitter side 11 and the receiver side 14. The rate of this attenuation depends rather heavily on whether there is water or another liquid condensed on the surface 18 of the oxide layer 17. As hereinbefore mentioned, the substrate 10 consists of piezoelectric material such as, for example, quartz, lithiumniobate, or the like. The mutual distance a between the finger patterns 12' and 13' depends upon the wavelength λ of the surface wave and is, for example, as follows:

$$A = \lambda/4;\ 3\lambda/4;\ 5\lambda/4;\ 7\lambda/4;\ \ldots$$

The wavelength λ is produced by the frequency f. The surface 18 is cooled in the following manner. Dew starts to form on the surface 18 as the relative humidity RH(T)

$$RH(T) = \exp\left\{ B\left[\frac{1}{T} + \frac{1}{T_o}\right] + C\log\left[\frac{T_o}{T}\right] \right\},$$

where B=6704.48, C=−4.71784, T=ambient temperature K. and T$_o$=dew point temperature, and said relative humidity is one. The temperature of the surface 18 is then T$_o$. When T$_o$ and T are known, RH(T) can be calculated via the foregoing equation.

The operation of the device of the invention is quantitatively described as follows. As the temperature of the substrate 10 comes close to the dew point temperature T$_o$, water, or some other liquid, begins to condense on the surface 18 of said substrate. The water, or other liquid is detected by an electronic detector 30 as an increase of the attenuation of the acoustic surface wave between the transmitter side 11 and the receiver side 14. The relative humidity RH can then be determined and, when required, directly indicated by an indicator 40, by the measurement of the dew point temperature T$_o$ and the ambient temperature T.

The method of the invention may also be undertaken in a manner such that there is no receiver side 14, 15, 16, and the measurement is based on a change of impedance $Z_{in}$ of the transmitter side 11, 12, 13 as the liquid condenses.

Figure 6:
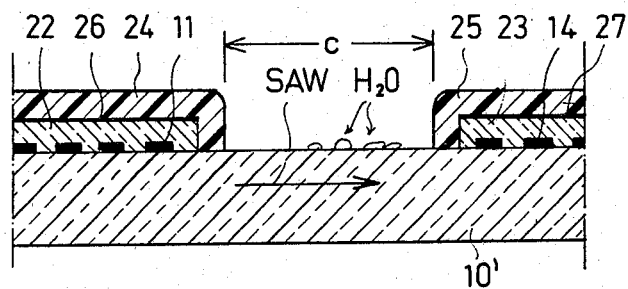
FIG. 6 is part of a cross-sectional view, on an enlarged scale, of another embodiment of the device of the invention.

In the embodiment of FIG. 6 of the dew point sensor, the substrate 10' is not piezoelectric material, but consists, for example, of a glass substrate. Piezoelectric films 22 and 23, consisting, for example, of ZnO, are provided on the electrodes 11 and 14. The electrodes 11 and 14 may be of the type shown in FIGS. 1 and 2. Metal membranes 26 and 27 are provided on the piezoelectric films 22 and 23. The piezoelectric films 22 and 23 are coated with protective films 24 and 25, consisting, for example, of SiO$_2$. As is apparent from FIG. 6, the acoustic surface wave SAW is transmitted between the transmitter and receiver electrodes 11 and 14 along the glass substrate 10'. There is an area a, on which there is no piezoelectric film, between the piezoelectric films 22 and 23, as shown in FIG. 6. Water may also be condensed in the area c and there it influences the transmission properties of the acoustic surface wave, in accordance with the invention.

The formation of dew on the surface of the LiNbO$_3$ substrate is described as follows. On an evenly cooled surface, the drops are evenly distributed until their size is approximately 5 microns. Thereafter, several drops combine to form larger drops. New small-sized drops are instantly formed in consequent free zones. When the surface is cooled down slowly, however, new drops are not formed. The drops keep on combining until the whole surface is covered with water.

The process is different on an impure surface. The impurities of the surface act as condensation centers at which drops of considerable size are formed before the formation of any perceivable drops on the rest of the surface, that is, before the dew point. As the drops combine to form larger drops, the contact angle between them and the surface becomes very large and the water layer becomes very thick before the water layer becomes continuous.

Figure 4:
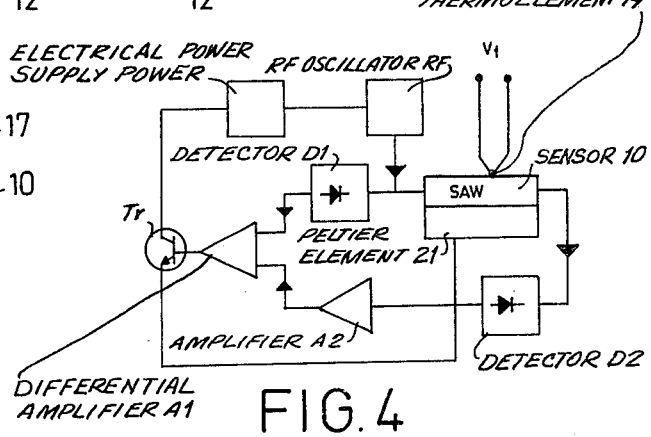
FIG. 4 is a block diagram of an embodiment of the electronic control unit of the device of the invention.

The electronic control unit of the heating and cooling systems of the moisture sensor of the invention is described with reference to FIG. 4. The temperature of the sensor 10 is measured by a thermoelement 19 (FIGS. 1 and 4). A Peltier element 21 is associated with the sensor 10 as a heating unit of said sensor. A relatively simple electronic unit is sufficient to control the temperature of the sensor 10, because of the high time constant of the thermal circuit formed by the Peltier element 21 and said sensor.

As is apparent from FIG. 4, a signal obtainable from a differential amplifier A1 is proportional to the difference between the input and output signals of the delay line. The attenuation detectors D1 and D2 and the amplification rate of the amplifier A2 is adjusted to balance the input of A1 as the difference of the input and output of the sensor 10 (SAW). This difference is, for example, 30 dB. Current is not then fed to the Peltier element 21.

The sensor 10 warms up, however, and dew begins to evaporate from its surface 18. This increases the input signal of the amplifier A1, and the current of the Peltier element 21 increases. The sensor 10 then cools down until enough dew has condensed to adjust the attenuation at the 30 dB level. When testing the aforedescribed device, its function was noted to be cyclic. This was due to the accumulation of humid air above the surface of the sensor, which caused the measured dew point temperature to deviate considerably from the real dew point temperature. A variation made in the device was the installation of a blower to blow the frozen air from above the sensor. After such installation, the operation was continuous and the dew point was followed very accurately.

Figure 8:
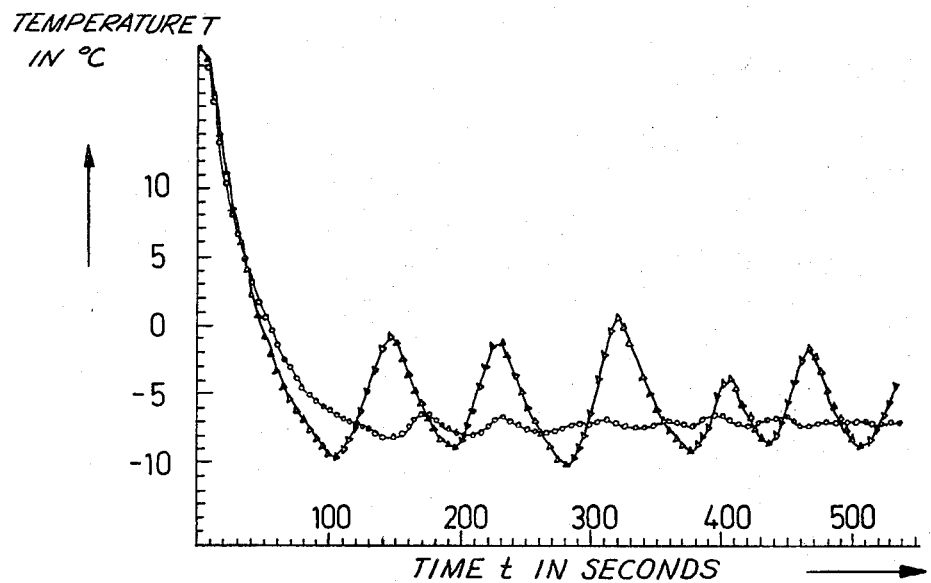
FIG. 8 is a graphic presentation of the operation of the sensor as a function of time, with the device of the invention ventilated and with the device of the invention non-ventilated.

The operation of the device both when ventilated and not ventilated is graphically illustrated in FIG. 8. In FIG. 8, the line formed by triangles illustrates the operation of the device without ventilation. A cyclic variation of the temperature of the sensor as a function of time is clearly seen. The line formed by circles illustrates the operation of the device when ventilated. It is seen that temperature variations are rather small. In FIG. 8, the abscissa represents the time t in seconds and the ordinate represents the temperature T in degrees C.

The Peltier element 21 needs a strong current of approximately 5 A, at a low voltage of approximately 2 V. One power transistor Tr is sufficient to control the current, and the base current of said power transistor is obtained from the booster of the amplifier A1. The amplifiers A1 and A2 may comprise operational amplifiers. The detectors D1 and D2 are usual diode detectors. An ordinary LC oscillator may be used as the RF oscillator RF. Rather great demands are made on the electrical power supply POWER. The oscillator RF, the amplifiers A1 and A2, and the Peltier element 21 each require a different voltage level.

Figure 7:
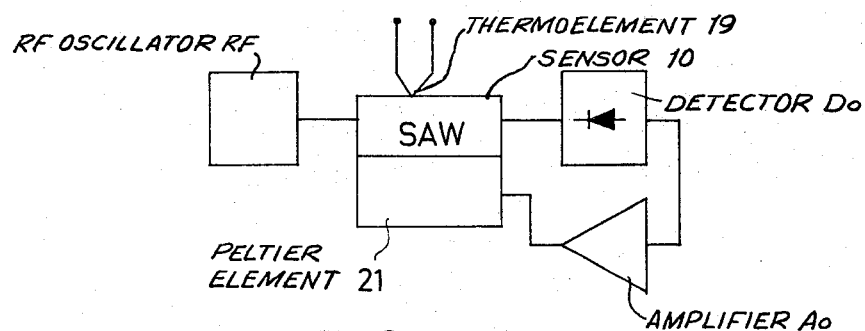
FIG. 7 is a block diagram of another embodiment of the electronic control unit of the device of the invention.

FIG. 7 shows another embodiment of the electronic control unit of the device of the invention. As is apparent from FIG. 7, the comparison signal shown in FIG. 4 is formed directly at the input of an amplifier Ao by constant tension potentiometers. Otherwise, the embodiments of FIGS. 7 and 4 are generally similar.

The sensitivity of the detector can be improved by using a pulse modulated RF signal. It is then possible to use a DC pre-current.

In experimenting in order to attempt to determine the influence of the dew on the impedance level and, consequently, on the unmatching attenuation, impedance measurements were made. Contrary to what was expected, the impedance is highly dependent upon the quantity of dew. Radiation resistance, which is a direct measurement of the surface wave transmission, dropped considerably as dew was formed. This implies that dew directly influences the formation of the surface wave as the mechanical boundary conditions change.

The change of input impedance $Z_{in}$ may be used directly for the detection of the dew point. It may be difficult, however, to provide a great and intensively responsive impedance in a large frequency band.

The electrode pattern may be protected against corrosion by coating the entire delay line with the layer 17 of $SiO_2$, for example. A thin insulating layer has only minute influence on the surface wave. The material selected also affects the dew formation. In order to obtain as low an insertion attenuation without dew as possible, the input and output may be tuned by an LC circuit.

The influence of the size of the dewdrops on the scattering at frequencies $f_1 = 37$ MHz and $f_3 = 109$ MHz is described with reference to FIGS. 5a, 5b and 5c.

Figure 5A:
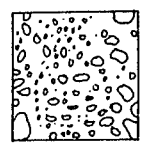
FIGS. 5a, 5b and 5c are views, on an enlarged scale, of dewdrops of various sizes.
Figure 5B:
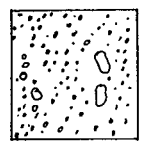
Figure 5C:
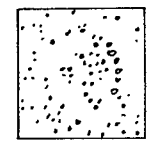

| FIG. 5a | FIG. 5b | FIG. 5c |
|---|---|---|
| A1 = 5 dB | 1 dB | 0.6 dB |
| A2 = 20 dB | 6 dB | 4 dB |

In FIGS. 5a, 5b and 5c, the large deviation of the drop size is a result of impurities on the surface 18 of the substrate 10.

The method of the invention eliminates cooling of the sensor by eliminating the cooling element used in association with the sensor. The device of the invention then detects condensation only, and provides an alarm in certain processes.

The aforedescribed method and the aforedescribed device with slight modifications may be used for following the quantity of water condensed in a certain time. Consequently, the aforedescribed device may be modified to function as an instrument for measuring the volatility and speed condensation. The electronic control unit of the device would then differ slightly from the aforedescribed electronic control unit. "Volatility" is meant to be the mass of water evaporated from a surface unit in a time unit. It is a complicated function of ambient temperature, relative humidity and flow speed. In agriculture and meteorology, for example, it is often useful to be able to measure the evaporating influence of the conditions in certain surroundings.

A volatility measuring instrument in accordance with the invention operates as follows. The surface 18 of the substrate 10 is cooled below the dew point temperature. Water is condensed in the path of the acoustic surface wave. The device is warmed up to the ambient temperature. Water begins to evaporate from the surface 18, and the attenuation rate of the acoustic surface wave is diminished. The period of time consumed as the attenuation of the acoustic surface wave decreases from one set value A1 to another set value A2 is measured. There is a simple dependence between the measured time and the volatility which can best be determined experimentally.

Favorable features or advantages of the device of the invention are its small size, the fact that the dew point can be measured simultaneously, and the independence of the device from an external liquid storage.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of dew point detection utilizing a piezoelectric sensor having a surface for detecting the presence of dew or other liquid, said method comprising the steps of
    producing an acoustic surface wave on the surface of the sensor;
    subjecting the surface of the sensor directly to the condensation and presence of dew and liquid to be detected thereby providing said condensation, dew and liquid directly on said surface and in contact with said acoustic wave;
    detecting said wave after transmission thereof across said surface; and
    measuring a parameter of the detected wave corresponding to the dew or liquid and thereby indicating the dew point or presence of liquid on said surface.

2. A method as claimed in claim 1, wherein said parameter is the attenuation of said wave and said attenuation varies in accordance with dew or liquid on said surface.

3. A method as claimed in claim 2, wherein said attenuation increases with increased dew or liquid and the increased attenuation is detected, and further comprising the steps of detecting and measuring the dew point temperature wherefrom the relative humidity may be determined.

4. A method as claimed in claim 2, further comprising the step of controlling the temperature of said sensor in a manner whereby said temperature increases and decreases cyclically on both sides of the dew point temperature.

5. A method as claimed in claim 2, further comprising the step of controlling the temperature of said sensor in response to measurement of said attenuation in a manner whereby said temperature is substantially continuous.

6. A device for dew point detection, comprising
    a piezoelectric sensor having a surface directly subjected to the condensation and presence of dew and liquid to be detected whereby said condensation, dew and liquid are provided directly on said surface;
    wave producing means for producing an acoustic surface wave on the surface of said sensor whereby said condensation, dew and liquid are in contact with said acoustic wave;
    detecting means for detecting said wave after transmission thereof across said surface; and
    measuring means for measuring a parameter of the detected wave corresponding to the dew or liquid and thereby indicating the dew point or presence of liquid on said surface.

7. A device as claimed in claim 6, wherein said sensor consists of material for transmitting elastic waves, said wave producing means including a transmitter for producing an acoustic surface wave in conjunction with piezoelectric phenomena of said sensor, and said detecting means including a receiver for receiving said wave, said wave being variably attenuated in transmission between said transmitter and receiver in accordance with dew or liquid on said surface, said measuring means measuring the attenuation of said wave.

8. A device as claimed in claim 7, wherein said attenuation increases with increased dew or liquid and said detecting means detects the increased attenuation, and further comprising temperature detecting and measuring means for detecting and measuring the dew point temperature wherefrom the relative humidity may be determined.

9. A device as claimed in claim 8, wherein said temperature detecting and measuring means comprises a thermoelement.

10. A device as claimed in claim 9, wherein said electrically insulating material consists of silicon dioxide and has a thickness in the range of 1000 to 3000 A.

11. A device as claimed in claim 7, further comprising temperature control means for controlling the temperature of said sensor in a manner whereby said temperature increases and decreases cyclically on both sides of the dew point temperature.

12. A device as claimed in claim 11, wherein said temperature control means comprises a Peltier element for cyclically cooling said sensor.

13. A device as claimed in claim 7, further comprising temperature control means for controlling the temperature of said sensor in a manner whereby said temperature is substantially continuous.

14. A device as claimed in claim 6, wherein said sensor consists of material for transmitting elastic waves and said wave producing means includes a transmitter for producing an acoustic surface wave in conjunction with piezoelectric phenomena of said sensor, and further comprising means for determining the input impedance of said transmitter, said input impedance varying in accordance with the dew point or presence of liquid on said surface.

15. A device as claimed in claim 6, wherein said wave producing means includes an electric oscillator having an oscillation frequency in the range of tens of megaHertz to hundreds of megaHertz.

16. A device as claimed in claim 6, wherein said sensor comprises a substrate having a surface which is said surface of said sensor, said wave producing means including a transmitter structure on said surface for producing an acoustic surface wave in conjunction with piezoelectric phenomena of said substrate and said detecting means including a receiver structure on said surface for receiving said wave, each of said transmitter and receiver structures comprising at least one electrode pattern of electrically conductive material and including contacts for supplying electrical energy to and deriving electrical energy from said sensor.

17. A device as claimed in claim 16, wherein the electrode patterns of said transmitter and receiver structures have electrodes and said transmitter structure includes a finger pattern between the electrodes of said electrode pattern of said transmitter structure, and said receiver structure includes a finger pattern between the electrodes of said electrode pattern of said receiver structure, the finger patterns of said transmitter and receiver structures being similar and spaced from each other.

18. A device as claimed in claim 17, further comprising a protective layer of electrically insulating material covering said electrode and finger patterns.

19. A device as claimed in claim 17, wherein the finger patterns of said transmitter and receiver structures are spaced from each other a distance equal to $\lambda/4, 3\lambda/4, 5\lambda/4, 7\lambda/4, \ldots$, where $\lambda$ is the wavelength of said wave.

20. A method of measuring the volatility of a liquid utilizing a piezoelectric sensor having a surface for detecting the volatility of a liquid, said method comprising the steps of producing an acoustic surface wave on the surface of the sensor;

subjecting the surface of the sensor directly to the presence of liquid the volatility of which is to be measured thereby providing said liquid directly on said surface and in contact with said acoustic wave;

detecting said wave after transmission thereof across said surface; and measuring a parameter of the detected wave corresponding to the liquid, said parameter being a factor in the determination of the volatility of liquid on said surface.

21. A method as claimed in claim 20, wherein said liquid is water, said wave is variably attenuated in transmission across said surface in accordance with water on said surface and said parameter is the attenuation of said wave, and further comprising the steps of cooling the temperature of said surface below the dew point whereby water condenses in the path of said wave, heating said surface to the ambient temperature whereby water begins to evaporate from said surface and the attenuation of said wave commences to diminish, and measuring the period of time during which the attenuation of said wave diminishes from one predetermined value to another, the measured time being another factor in the determination of the volatility.

22. A device for the detection of the volatility of a liquid, said device comprising a piezoelectric sensor having a surface directly subjected to a liquid the volatility of which is to be measured thereby providing said liquid directly on said surface;

wave producing means for producing an acoustic surface wave on the surface of said sensor thereby providing said liquid in contact with said acoustic wave;

detecting means for detecting said wave after transmission across said surface; and measuring means for measuring a parameter of the detected wave corresponding to the liquid, said parameter being a factor in the determination of the volatility of liquid on said surface.

23. A device as claimed in claim 22, wherein said liquid is water, said wave is variably attenuated in transmission across said surface in accordance with water on said surface and said measuring means measures the attenuation of said wave, and further comprising temperature control means for cooling the temperature of said surface below the dew point whereby water condenses in the path of said wave and for heating said surface to the ambient temperature whereby water begins to evaporate from said surface and the attenuation of said wave commences to diminish, and time measuring means for measuring the period of time during which the attenuation of said wave diminishes from one predetermined value to another, the measured time being another factor in the determination of the volatility.

* * * * *